(12) United States Patent
Nemoto et al.

(10) Patent No.: US 8,487,126 B2
(45) Date of Patent: Jul. 16, 2013

(54) PROCESS FOR PREPARATION OF DIETHYLENETRIAMINEPENTAACETIC ACID DERIVATIVE, AND DIETHYLENETRIAMINEPENTAACETIC ACID DERIVATIVE

(75) Inventors: Hisao Nemoto, Tokushima (JP); Tomoyuki Kawamura, Tokushima (JP); Kenji Yatsuzuka, Tokushima (JP); Masaki Kamiya, Tokushima (JP)

(73) Assignee: The University of Tokushima, Tokushima (JP)

( * ) Notice: Subject to any disclaimer, the term of this patent is extended or adjusted under 35 U.S.C. 154(b) by 0 days.

(21) Appl. No.: 13/499,724

(22) PCT Filed: Sep. 22, 2010

(86) PCT No.: PCT/JP2010/066438
§ 371 (c)(1),
(2), (4) Date: Apr. 2, 2012

(87) PCT Pub. No.: WO2011/046007
PCT Pub. Date: Apr. 21, 2011

(65) Prior Publication Data
US 2012/0203027 A1    Aug. 9, 2012

(30) Foreign Application Priority Data
Oct. 15, 2009    (JP) ................................ 2009-238696

(51) Int. Cl.
C07C 69/34    (2006.01)
C07C 229/00    (2006.01)

(52) U.S. Cl.
USPC ........................................ 560/190; 560/169

(58) Field of Classification Search
None
See application file for complete search history.

(56) References Cited

U.S. PATENT DOCUMENTS

| | | |
|---|---|---|
| 5,714,591 A | 2/1998 | Yamamoto et al. |
| 5,780,670 A | 7/1998 | Yamamoto et al. |
| 5,888,476 A | 3/1999 | Woulfe |
| 5,961,953 A | 10/1999 | Woulfe |
| 6,040,432 A | 3/2000 | Krause et al. |
| 6,254,850 B1 | 7/2001 | Krause et al. |
| 6,617,332 B1 | 9/2003 | Brands et al. |
| 2002/0164289 A1 | 11/2002 | McMurry et al. |
| 2003/0180223 A1 | 9/2003 | McMurry et al. |
| 2004/0202613 A1 | 10/2004 | McMurry et al. |
| 2004/0208827 A1 | 10/2004 | McMurry et al. |
| 2007/0003479 A1 | 1/2007 | McMurry et al. |
| 2007/0020184 A1 | 1/2007 | McMurry et al. |
| 2007/0020185 A1 | 1/2007 | McMurry et al. |

FOREIGN PATENT DOCUMENTS

| | | |
|---|---|---|
| JP | 9-31037 A | 2/1997 |
| JP | 9-31078 A | 2/1997 |
| JP | 10-513445 A | 12/1998 |
| JP | 11-501012 A | 1/1999 |
| JP | 2001-504120 A | 3/2001 |

OTHER PUBLICATIONS

Database CAPLUS Chemical Abstracts Service, Columbus, Ohio, US; Database Accession No. 2011:82621, Abstract of Giovenzana et al., Organic & Biomolecular Chemistry (2011).*
Arnelli et al., "Conjugates of Gadolinium Complexes to Bile Acids as Hepatocyte-Directed Contrast Agents for Magnetic Resonance Imaging", J. Med. Chem., 2004, vol. 47, pp. 3629-3641.
Keana et al., "Chelating Ligands Functionalized for Facile Attachment to Biomolecules. A Convenient Route to 4-Isothiocyanatobenzyl Derivatives of Diethylenetriaminepentaacetic Acid and Ethylenediaminetetraacetic Acid", J. Org. Chem., 1990, vol. 55, pp. 2868-2871.
Williams et al., "Synthesis of Enantiomerically Pure Diethylenetriaminepentaacetic Acid Analogues. L-Phenylalanine as the Educt for Substitution at the Central Acetic Acid", J. Org. Chem., 1993, vol. 58, pp. 1151-1158.
Laurent et al., "Relaxivity and Transmetallation Stability of New Benzyl-Substituted Derivatives of Gadolinium-DTPA Complexes", Helvetica Chimica Acta, 2004, vol. 87, pp. 1077-1089.
Chen et al., "Simple, Clickable Protocol for Atomic Force Microscopy Tip Modification and Its Application for Trade Ricin Detection by Recognition Imaging", Langmuir, 2009, vol. 25, pp. 2860-2864.
International Search Report of PCT/JP2010/066438.

* cited by examiner

*Primary Examiner* — Karl J Puttlitz
(74) *Attorney, Agent, or Firm* — Bacon & Thomas, PLLC

(57) ABSTRACT

The objective of the present invention is to provide a process for simple and efficient preparation of an intermediate compound to synthesize a gadolinium complex having a substituent for improving a retention property in blood time and specificity to an intended organ. The objective of the present invention is also to provide an intermediate compound produced by the said production process. The process for preparation of the diethylenetriaminepentaacetic acid derivative (I):

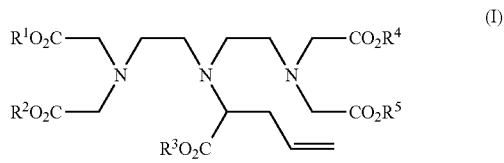

wherein $R^1$ to $R^5$ are independently $C_{1-6}$ alkyl groups;
comprising the steps of:
reacting a diethylenetriaminepentaacetic acid pentaester with a halogenated ally compound in an aprotic solvent;
removing the excess halogenated ally compound (III); and
reacting a reaction product of the diethylenetriaminepentaacetic acid pentaester and the halogenated ally compound with a base in a solvent.

9 Claims, No Drawings

PROCESS FOR PREPARATION OF DIETHYLENETRIAMINEPENTAACETIC ACID DERIVATIVE, AND DIETHYLENETRIAMINEPENTAACETIC ACID DERIVATIVE

TECHNICAL FIELD

The present invention relates to a process for producing a diethylenetriaminepentaacetic acid derivative, and a diethylenetriaminepentaacetic acid derivative.

BACKGROUND ART

A magnetic resonance imaging diagnosis, i.e., MRI, is receiving plenty of attention, since any cross-sectional image of human body can be taken using magnetism and radiowave. In a MRI, a contrast agent for MRI, such as Magnevist (registered trademark, generic name: meglumine gadopentetate), is sometimes used in order to obtain a clearer and more detailed image.

Magnevist, by which the contrast of an image can be improved, has a highly toxic gadolinium ion. In the chemical structure thereof, the gadolinium ion is chelated by DTPA: DiethyleneTriaminePentaacetic Acid as follows so that the toxicity is neutralized.

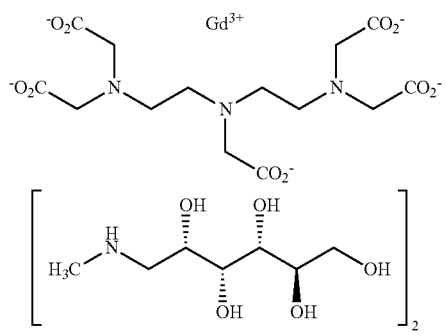

Magnevist rapidly diffuses out into a living body after administration, and then is eliminated in urine. Such a property is preferable in terms of safety; however, a retention property in blood for a longer time and specificity to an intended organ are also needed for diagnosis.

For the above-described property, it can be thought that a substituent for improving a retention property in blood and specificity to an intended organ is bound to DTPA through the carboxy groups thereof (Non-patent Document 1). However, such a modification increases the probability of spread of naked gadolinium ion having high toxicity in a living body, since the number of carboxy groups, which can chelate gadolinium ion, is decreased.

Contrary to the above method, another method has been developed (Patent Documents 1 to 4 and Non-patent Documents 1 to 4). In the method, a substituent for improving a retention property in blood and the like is bound to the methylene group located between the carboxyl group and the amino group. The methylene group plays no role in the chelate to a gadolinium ion.

However, the target compound cannot be efficiently produced in the above conventional methods.

Specifically, for example, in the method described in Patent Document 3, Non-patent Documents 1, 3 and 4, a low-molecular compound having a substituent for improving a retention property in blood and the like or a precursor substituent thereof is reacted with other amine compounds and carboxy compounds to synthesize a DTPA derivative as the following scheme.

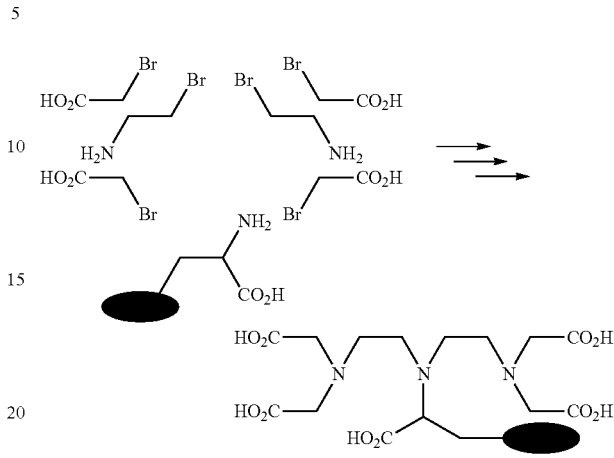

However, such a synthetic process requires many steps, and has problems of high cost and environmental deterioration. For example, a lot of waste substances such as halide ion salt are produced.

In Example described in Patent Document 4, a DTPA derivative having a reactive substituent is used as a starting compound, but the production method thereof is not explicitly described. The derivative may be probably produced by a similar method to the above.

In the method described in Patent Documents 1 and 2 and Non-patent Document 2, a substituent is bound to a DTPA ester in the presence of a base.

However, it is difficult according to the method to bond a substituent to an intended position only. In addition, a side reaction by which multiple substituents are bound is induced. Therefore, the yield of the target compound is low.

PRIOR ART DOCUMENT

Patent Documents
   Patent Document 1: JP-A-9-31037
   Patent Document 2: JP-A-9-31078
   Patent Document 3: JP-T-10-513445
   Patent Document 4: JP-T-2001-504120
Non-Patent Documents
   Non-patent Document 1: Pier Lucio Anelli et al., Journal of Medicinal Chemistry, vol. 47, pp. 3629-3641 (2004)
   Non-patent Document 2: John F. W. Keana et al., Journal of Organic Chemistry, vol. 55, no. 9, pp. 2868-2871 (1990)
   Non-patent Document 3: Matthew A. Williams et al., Journal of Organic Chemistry, vol. 58, no. 5, pp. 1151-1158 (1993)
   Non-patent Document 4: Sophie Laurent et al., Helvetica Chimica Acta, vol. 47, pp. 1077-1089 (2004)

SUMMARY OF THE INVENTION

Problems to be Solved by the Invention

As described above, various DTPA derivatives have been developed, which DTPA derivatives are gadolinium complexes used for contrast agents for MRI and are substituted with a substituent for improving a retention property in blood and specificity to an intended organ.

However, the conventional processes for producing the above derivatives require many reaction steps, the total yield of the processes is very low and a lot of by-product are produced in the processes; therefore, the above derivatives cannot be produced in an industrial scale.

Under such a circumstance, the objective of the present invention is to provide a process for simple and efficient preparation of an intermediate compound to synthesize a gadolinium complex having a substituent for improving a retention property in blood time and specificity to an intended organ. The objective of the present invention is also to provide an intermediate compound produced by the said production process.

Solutions to the Problems

The present inventors carried out intensive study and research for solve the above problems. As a result, the present inventors found that a reactive substituent can be very easily and efficiently bound to the specific position of a DTPA ester by a Stevens transfer reaction in three steps, though a Stevens transfer reaction is conventionally carried out in one step and such a Stevens transfer reaction in three steps has no precedent.

The process for preparation of a diethylenetriaminepentaacetic acid derivative according to the present invention is characterized in that;

the diethylenetriaminepentaacetic acid derivative is represented by the following formula (I):

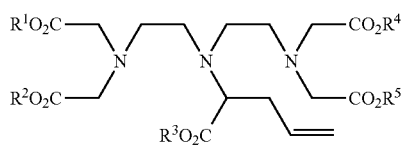

wherein $R^1$ to $R^5$ are independently $C_{1-6}$ alkyl groups;
comprising the steps of:
reacting a diethylenetriaminepentaacetic acid pentaester represented by the following formula (II) with a halogenated ally compound represented by the following formula (III) in an aprotic solvent:

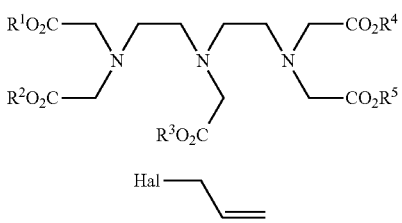

wherein $R^1$ to $R^5$ have the same meaning as the above; and "Hal" is a halogen atom;
removing the excess halogenated ally compound (III); and
reacting a reaction product of the diethylenetriaminepentaacetic acid pentaester (II) and the halogenated ally compound (III) with a base in a solvent.

The diethylenetriaminepentaacetic acid derivative according to the present invention is characterized in being represented by the following formula (I):

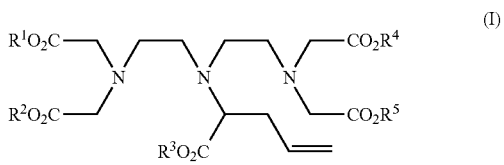

wherein $R^1$ to $R^5$ are independently $C_{1-6}$ alkyl groups.

The gadolinium complex precursor according to the present invention is characterized in being represented by the following formula (IV):

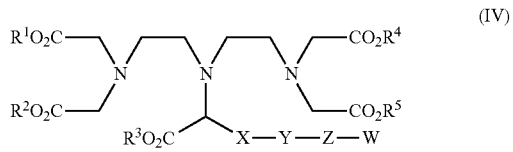

wherein
$R^1$ to $R^5$ are independently $C_{1-6}$ alkyl groups;
X is —$(CH_2)_3$— or —$CH_2$—CH=CH—;
Y is a $C_{6-12}$ arylene group, —CH=CH— or —$(CH_2)_2$—;
Z is a $C_{1-6}$ alkylene group, an amino group, an ether group, a carbonyl group, an ester group, an amide group, a urea group, or a group formed by linearly-bonding not less than two the said groups;
W is —CH=$CH_2$, —CH≡CH, an amino group, a carboxy group, an active amide group, an active ester group or a halogen atom.

To the gadolinium complex precursor, a substituent for improving a retention property in blood and specificity to an intended organ is bound through the above "W"; and then, the ester groups are hydrolyzed and a gadolinium ion is coordinated. The obtained compound can be used as a contrast agent for MRI.

In the present invention, the term "a $C_{1-6}$ alkyl group" means a straight or branched chain aliphatic hydrocarbon group having 1 to 6 carbon atoms, such as a methyl group, an ethyl group, a n-propyl group, an isopropyl group, a n-butyl group, a sec-butyl group, a t-butyl group, a pentyl group and a hexyl group. The group is preferably a $C_{1-4}$ alkyl group, and more preferably a $C_{1-2}$ alkyl group.

The "halogen atom" can be exemplified by a fluorine atom, a chlorine atom, a bromine atom and an iodine atom; and is preferably a chlorine atom or a bromine atom, and most preferably a bromine atom.

The term "a $C_{6-12}$ arylene group" means a bivalent aromatic hydrocarbon group having 6 to 12 carbon atoms, such as a phenylene group, an indenylene group, a naphthylene group and a biphenylene group. The group is preferably a phenylene group or a naphthylene group, and more preferably a phenylene group.

The term "a $C_{1-6}$ alkylene group" means a bivalent straight or branched chain aliphatic hydrocarbon group having 1 to 6 carbon atoms, such as a methylene group, a dimethylene group, a trimethylene group, a methyldimethylene group, a tetramethylene group, a 1-methyltrimethylene group, a 1,1-dimethyldimethylene group, a pentamethylene group and a hexamethylene group. The group is preferably a $C_{1-4}$ alkylene group, and more preferably a $C_{1-2}$ alkylene group.

The term "an amino group" in the definition of "Z" is —NH—; the term "an amino group" in the definition of "W" is —$NH_2$; the term "an ether group" is —O—; the term "a carbonyl group" is —C(=O)—; the term "an ester group" is —C(=O)O— or —OC(=O)—; the term "an amide group" is —NHC(=O)— or —C(=O)NH—; and the term "a urea group" is —NHC(=O)NH—.

The terms "an active amide group" and "an active ester group" in the definition of "W" are respectively an amino group and a carboxy group of which reactivity is increased for easily-bonding a substituent for improving a retention property in blood and specificity to an intended organ. The groups can be exemplified by a phthalimide group, which is also referred to as a dioxoazolinyl group, a 5-norbornene-2,3-dicarbimide group, a N-hydroxysuccinimide ester group and a 4-nitrophenylester group.

The groups of "Z" and "X-Y-Z" play a role as a linker group; and it can be prevented by the groups that the approach of the contrast agent for MRI to an intended organ is inhibited by a bulky gadolinium complex part, and it can become easy by the groups to synthesize the compound. When "Z" consists of two or more groups, the number of the groups is preferably not more than 5, since the length of the linker group should be appropriate.

MODES FOR CARRYING OUT THE INVENTION

Hereinafter, the present invention process is described in the order of operation.

(1) The First Step

In the present invention process, first, the diethylenetriaminepentaacetic acid pentaester (II) is reacted with the halogenated ally compound (III) in an aprotic solvent. In the first step, it is thought that the reaction proceeds as follows.

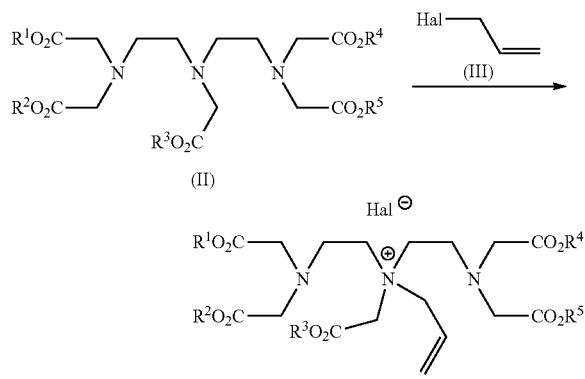

When the diethylenetriaminepentaacetic acid pentaester (II) is reacted with a strong base as conventional processes, the halogenated allyl compound (III) cannot be bound to the desired position since a positional specificity is lost, and multiple halogenated allyl compounds (III) are bound. On the other hand, when a weak base is used, an anion at the α-position of the ester group cannot be obtained. For the above-described reasons, the position and the number of the halogenated allyl compound (III) to be bound cannot be controlled by conventional processes.

On the other hand, in the first step of the present invention, the diethylenetriaminepentaacetic acid pentaester (II) is reacted with the halogenated allyl compound (III) without using a base. As a result, the halogenated allyl compound (III) is bound to only the central amino group of which reactivity is slightly higher than those of the other amino groups. The reason why such a result can be obtained is that the above resultant compound is the most stable and the other compounds are also turned out to be the above resultant compound even if the halogenated allyl compound (III) is bound to the other amino groups or the multiple compounds (III) are reacted, since the above reaction is reversible. It is amazing that the position or the number of the halogenated allyl compound (III) can be controlled by such a simple condition.

If the diethylenetriaminepentaacetic acid pentaester (II) as the starting compound of the present invention process is commercially available, the commercial product can be used. Alternatively, the pentaester (II) can be synthesized by esterizing a commercially available diethylenetriaminepentaacetic acid according to a conventional method. It is preferable that $R^1$ to $R^5$ in the diethylenetriaminepentaacetic acid pentaester (II) are the same for the reasons of easy synthesis.

The halogenated allyl compound (III) has a simple structure. Therefore, the compound (III) can be synthesized according to a conventional method well-known to the person skilled in the art. Alternatively, if the compound (III) is commercially available, the commercial product can be used.

The first step is carried out in an aprotic solvent. In the reaction of the first step, the lone electron pair of the amino group in the diethylenetriaminepentaacetic acid pentaester (II) nucleophilicly attacks. Therefore, an aprotic solvent, by which an amino group is not solvated, is used. In addition, a protic solvent has problems that the main reaction may be inhibited and the halogenated allyl compound as the starting compound is wasted, since a protic solvent reacts with the halogenated allyl compound.

It is preferred that such an aprotic solvent can adequately dissolve the starting compounds. The aprotic solvent is exemplified by an amide aprotic solvent such as dimethylformamide and dimethylacetamide; an ether aprotic solvent such as diethylether, cyclopentyl methyl ether, tetrahydrofuran and dimethoxyethane; a sulfoxide aprotic solvent such as dimethylsulfoxide; a ketone aprotic solvent such as acetone and t-butyl methyl ketone; a nitrile aprotic solvent such as acetonitrile; a halogenated hydrocarbon aprotic solvent such as dichloromethane and chloroform; an aromatic hydrocarbon aprotic solvent such as benzene and toluene; and others.

The concentration of the diethylenetriaminepentaacetic acid pentaester (II) in the reaction mixture of the first step may be appropriately adjusted; and is preferably not less than 10 g/L, since when the concentration is high, the reaction may readily proceeds. On the other hand, the upper limit of the concentration is not particularly limited, but the concentration is preferably not more than 200 g/L due to requisite amount of the diethylenetriaminepentaacetic acid pentaester (II).

In the first step, it is preferred that a large excess amount of halogenated allyl compound (III) relative to the diethylenetriaminepentaacetic acid pentaester (II) is used. As a result, the reaction equilibrium is shifted toward the above resultant compound side, and the reaction is accelerated. It is preferred to use not less than 5 times by mole of the halogenated allyl compound (III) relative to the diethylenetriaminepentaacetic acid pentaester (II). On the other hand, use of too excess of the halogenated allyl compound (III) has only limited effects; therefore, the above ratio is preferably not more than 15 times by mole. The above ratio is more preferably not less than 7 times by mole, since the present inventors found by experiment that when the above ratio is adjusted to 9 times by mole or more, the effect is not increased according to the value. However, if very inexpensive halogenated allyl compound (III) can be obtained, the above ratio may be 9 times by mole or more. The upper limit of the above ratio is not limited, but the above ratio is preferably not more than 15 times by mole, and more preferably not more than 10 times by mole.

The temperature of the reaction may be appropriately adjusted, and is preferably not less than 20° C. and not more than 60° C., and more preferably not less than 30° C. and not more than 50° C.

The reaction time may be set up by preliminary experiment, or the reaction is continued until it is confirmed by reverse phase HPLC and the like that the total diethylenetriaminepentaacetic acid pentaester (II) is used. The reaction time is preferably not less than 1 hour and not more than 80 hours, and more preferably not less than 5 hours and not more than 60 hours.

(2) The Second Step

Next, the excess halogenated ally compound (III) is removed. If the halogenated allyl compound (III) remains in the next step, the remaining allyl compound (III) is further reacted with the reaction product of the diethylenetriaminepentaacetic acid pentaester (II) and the halogenated allyl compound (III). The second step is carried out for preventing such a side reaction from occurring.

With respect to the boiling point of the halogenated allyl compound (III), the boiling point of allyl bromide is 70~71° C. and that of ally iodide is 102~103° C. Therefore, the reaction mixture may be concentrated under reduced pressure for removing the halogenated allyl compound (III). In the second step, the solvent may be also distilled away.

The halogenated allyl compound (III) may not be completely removed. In other words, the allyl compound (III) may be removed to such an extent that side reaction does not occur in the next step. However, the halogenated allyl compound (III) should be removed as much as possible to prevent by-product bound with two or more allyl groups. Therefore, for example, the following procedure may be repeated two or three times:

the reaction mixture is concentrated under reduced pressure;
appropriate amount of an aprotic solvent is further added to dissolve the resultant viscous liquid; and
the mixture is concentrated under reduced pressure.

(3) The Third Step

Next, the reaction product of the diethylenetriaminepentaacetic acid pentaester (II) and the halogenated ally compound (III) is reacted with a base in a solvent. In the third step, it is thought that the following transfer reaction may occur.

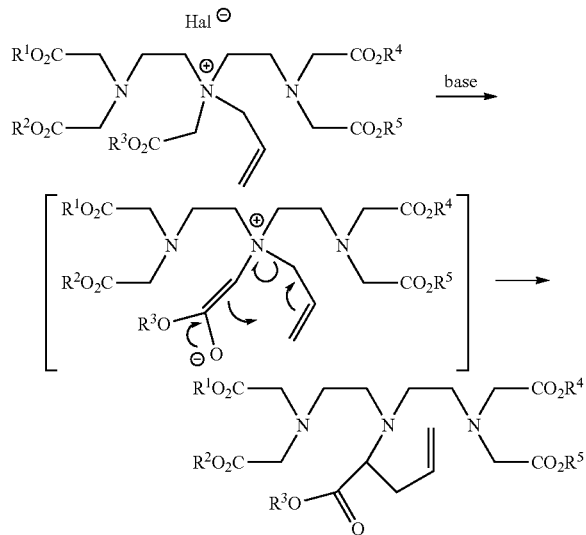

After the second step, an aprotic solvent may remain in some cases; however, the solvent is usually removed completely or in large part with the halogenated allyl compound (III). Therefore, a solvent is preferably added to smoothly progress the reaction.

The solvent used in the third step is not limited as long as it has appropriate solubility for dissolving the substrate compounds and does not inhibit the reaction. For example, the solvent is exemplified by the aprotic solvent exemplified in the description of the second step; an aliphatic hydrocarbon solvent such as hexane; an ester solvent such as ethyl acetate; an alcohol solvent such as methanol and ethanol; and the others. When an alcohol solvent is used, the same alcohol as the alcohol in the acetic acid ester group of the substrate compound is preferably used, since a transesterification reaction may possibly occur.

The amount of the solvent to be used may be appropriately adjusted, and the concentration of the reaction mixture obtained in the second step may be not less than 2 w/v % and not more than 20 w/v % in order to smoothly accelerate the reaction.

After the reaction mixture obtained in the second step is dissolved or dispersed in a solvent, a base is added. The kind of the base is not particularly limited, and is exemplified by an alkali metal carbonate such as potassium carbonate and sodium carbonate; an alkaline earth metal carbonate such as calcium carbonate and magnesium carbonate; an alkali metal hydrogencarbonate such as potassium hydrogencarbonate and sodium hydrogencarbonate; an alkaline earth metal hydrogencarbonate such as calcium hydrogencarbonate and magnesium hydrogencarbonate; an alkali metal hydroxide such as potassium hydroxide and sodium hydroxide; an alkali metal hydride such as sodium hydride; an organic amine such as triethylamine and pyridine; an alkali metal alkoxide such as sodium ethoxide and potassium ethoxide; and others. When a strong base such as sodium hydroxide is used, a hydrolysis reaction may possibly proceed. In addition, when metal alkoxide is used, an alcohol exchange reaction may possibly occur. Therefore, it is preferred that a weak base such as a carbonate or a hydrogencarbonate of an alkali metal or alkaline earth metal.

The amount of the base to be used may be appropriately adjusted, and it is preferred that the base is excessively used at least compared to the amount necessary for neutralizing a halogen anion which is a counter anion of the ammonium cation generated by reacting the diethylenetriaminepentaacetic acid pentaester (II) and the halogenated allyl compound (III). Specifically, it is preferred to use the base of about not less than 0.5 times by mole and about not more than 1.2 times by mole of the halogenated allyl compound (III) to be used.

The temperature of the reaction may be appropriately adjusted, and is preferably about not less than 50° C. and about not more than 100° C., and the third step may be carried out under reflux.

The reaction time may be set up by preliminary experiment, or the reaction is continued until it is confirmed by reversed phase HPLC and the like that the total reaction product of the diethylenetriaminepentaacetic acid pentaester (II) and the halogenated allyl compound (III) is used. The reaction time is preferably about not less than 10 hours and about not more than 100 hours, and more preferably about not less than 50 hours and about not more than 80 hours.

After the reaction, the diethylenetriaminepentaacetic acid derivative (I) as the target compound may be purified by a conventional method. For example, when potassium carbonate or the like is used, water is generated. In such a case, after the target compound is extracted using a water-insoluble solvent such as ethyl acetate and chloroform, the extract is washed with brine, diluted hydrochloric acid, water or the like. The extract is dried with anhydrous magnesium sulfate, anhydrous potassium carbonate or the like, and then concentrated. Next, purification procedure is carried out from the concentrate by silica gel column chromatography, recrystallization or the like.

As described above, the diethylenetriaminepentaacetic acid derivative (I) can be produced very efficiently, since the present invention process includes only a few steps and can be carried out easily.

The diethylenetriaminepentaacetic acid derivative (I) according to the present invention has a reactive allyl group. Therefore, for example, the derivative (I) can be subjected to a coupling reaction with a halogenated vinyl compound or a halogenated aryl compound which have a reactive functional group or a protected reactive functional group in the presence of a palladium catalyst. Further, through the bound vinyl compound or aryl compound as a linker group, a substituent for improving a retention property in blood and specificity to an intended organ can be bound. Alternatively, a substituent for improving a retention property in blood and the like can be directly bound to the diethylenetriaminepentaacetic acid derivative (I) according to the present invention.

Specifically, for example, the gadolinium complex precursor (IV) according to the present invention can be produced from the diethylenetriaminepentaacetic acid derivative (I) according to the present invention as the following scheme.

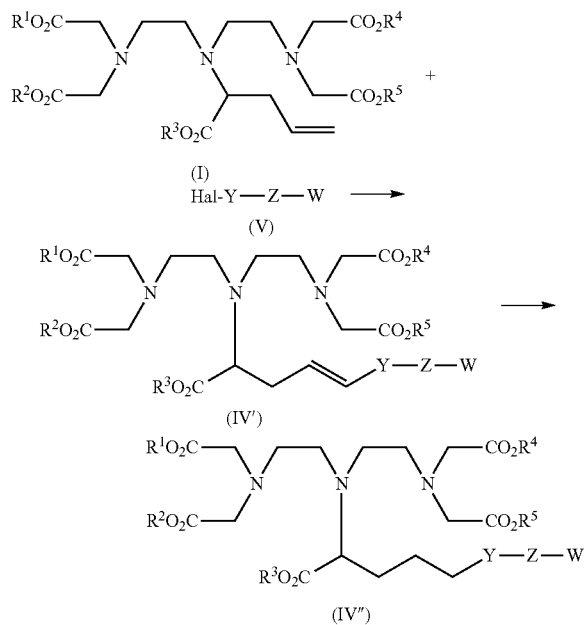

The halogenated compound (V) in the above scheme can be readily produced by the person skilled in the art. The "W" may be protected by a protective group such as a BOC group, which does not inhibit the reaction and can be easily cleaved.

In the above reaction, the diethylenetriaminepentaacetic acid derivative (I) and the halogenated compound (V) are reacted in the presence of a palladium catalyst in a solvent which can appropriately dissolved the said compounds. Further, the ethenyl group (—CH═CH—) may be reduced by a conventional method.

To the above-described gadolinium complex precursor (IV), a substituent for improving a retention property in blood and specificity to an intended organ is bound through the "W"; and then, the ester group is hydrolyzed and a gadolinium ion is coordinated. The obtained compound can be used as a contrast agent for MRI. Therefore, the diethylenetriamine pentaacetic acid derivative (I) and the gadolinium complex precursor (IV) according to the present invention is very useful as am intermediate compound for producing a contrast agent for MRI which has a retention property in blood and specificity to an intended organ.

EXAMPLES

Hereinafter, the present invention is described in more detail with Examples; however, the present invention is not limited to the following Examples in any way, and some of the details can be variously changed in accordance with the description of the present specification. The changed embodiment is also included in the scope of the present invention.

Synthesis Example 1

Synthesis of ethyl 2-[N,N-bis(2-{(N',N'-bis[(ethoxycarbonyl)methyl]amino}ethyl)amino]pento-4-enolate

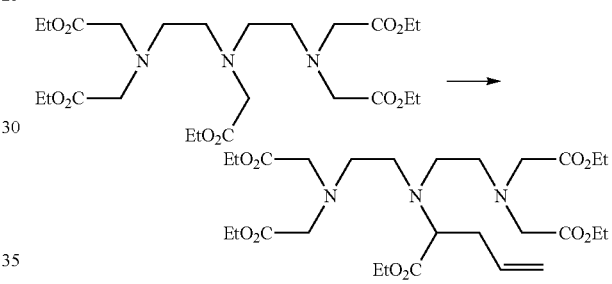

Diethylenetriaminepentaacetic acid pentaethyl ester as a starting compound (7 g, 13.1 mmol) was dissolved in DMF (175 mL). To the solution, allyl bromide (10.2 mL, 118.1 mmol) was added at room temperature. The mixture was stirred at 40° C. for 39 hours. Next, the mixture was concentrated under reduced pressure. To the obtained concentrate, DMF (175 mL) and potassium carbonate (16.3 g, 118.1 mmol) were added. The mixture was stirred at 80° C. for 70 hours. The mixture was cooled down to room temperature, and then a saturated aqueous solution of sodium hydrogencarbonate (300 mL) was added thereto. Extraction procedures from the obtained mixture were carried out three times using ethyl acetate (300 mL). The extract was washed with saturated saline (200 mL), and then was dried with anhydrous potassium carbonate. The extract was concentrated under reduced pressure. The target compound was obtained as a yellow oil from the concentrate (yield: 4.8 g, 8.3 mmol, 63%, yield based on inversion rate of the starting compound: 70%) by purification procedure using silica gel column chromatography (eluent: hexane/ethyl acetate=1:1).

FT-IR (neat, cm$^{-1}$): 3628, 3448, 3077, 2981, 2366, 2055, 1732, 1446, 1370, 1343, 1188, 1029, 917, 856, 808, 733

$^1$H-NMR (CDCl$_3$, 400 MHz): δ 5.80 (ddt, J=16.8, 10.0, 6.8 Hz, 1H), 5.08 (d, J=16.8 Hz, 1H), 5.03 (dt, J=10.0, 0.4 Hz, 1H), 4.20-4.13 (m, 10H), 3.57 (s, 8H), 3.50 (t, J=7.6 Hz, 1H), 2.88-2.77 (m, 6H), 2.71-2.66 (m, 2H), 2.51 (ddd, J=14.0, 7.6, 6.8 Hz, 1H), 2.35 (ddd, J=14.0, 7.6, 6.8 Hz, 1H), 1.285 (t, J=6.8 Hz, 12H), 1.276 (t, J=6.8 Hz, 3H)

$^{13}$C-NMR (CDCl$_3$, 100 MHz): δ 172.2 (C), 170.9 (C×4), 134.9 (CH), 116.5 (CH$_2$), 63.6 (CH), 60.2 (CH$_2$×4), 60.0

(CH$_2$), 55.1 (CH$_2$×4), 53.3 (CH$_2$×2), 50.2 (CH$_2$×2), 34.3 (CH$_2$×2), 14.3 (CH$_3$), 14.1 (CH$_3$×4)

EI-HRMS: m/z (M+H$^+$) calculated value (C$_{27}$H$_{48}$N$_3$O$_{10}$): 574.3340, measured value: 574.3331

Synthesis Example 2

(1) Synthesis of t-butyl[2-(4-iodophenyl)ethyl]carbamate

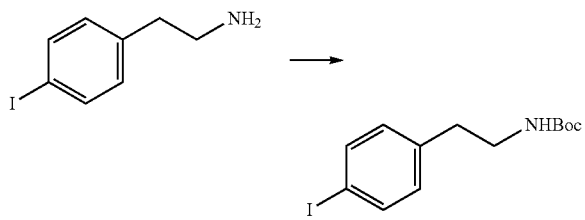

In THF (50 mL), 2-(4-iodophenyl)-1-ethylamine (6.59 g, 26.7 mmol) was dispersed. In the dispersion, triethylamine (3.7 mL, 26.7 mmol) and dicarbonic acid di(t-butyl) ester (5.8 g, 26.7 mmol) were added. The mixture was stirred at room temperature for 1 hour. Ethyl acetate and water were added to the mixture. The organic layer was separated, and washed with water and sodium chloride solution sequentially. The organic layer was dried with potassium carbonate, and then concentrated. The target compound (9.3 g) was obtained as a colorless needle crystal.

(2) Ethyl (4E)-2-[N,N-bis[2-[N',N'-bis[(ethoxycarbonyl)methyl]amino]ethyl]amino]-5-(4-[(2-[(t-butoxy)carbonylamino]ethyl]phenyl)pento-4-enolate

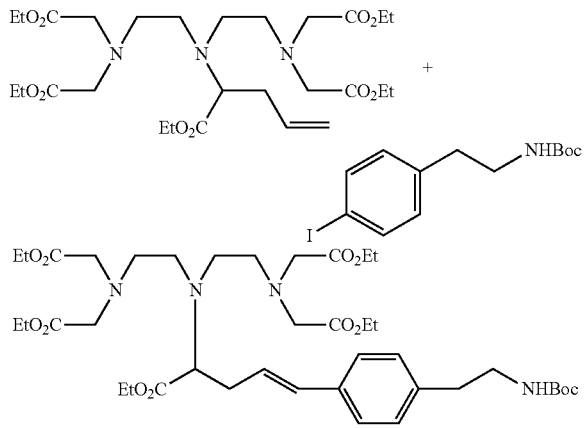

The ethyl 2-[N,N-bis(2-{N',N'-bis[(ethoxycarbonyl)methyl]amino}ethyl)amino]pento-4-enolate (100 mg, 0.522 mmol) obtained in the above Synthesis Example 1 was dissolved in a mixed solvent of DMF/water=10/1 (1.1 mL). In the solution, the iodophenyl compound (185.6 mg, 0.522 mmol) synthesized in the above Synthesis Example 2(1) and diisopropylethylamine (46.7 µL, 0.261 mmol) were added at room temperature. The mixture was heated up to 60° C. Then, bis(acetonitrile)dichloropalladium (4.52 mg, 0.0174 mmol) was added thereto, and the mixture was stirred at 60° C. for 11 hours. The mixture was filtered through silica gel, and the filtrate was concentrated under reduced pressure. The target compound was obtained as a yellow oil from the concentrate by purification procedure using silica gel column chromatography (eluent: hexane/ethyl acetate=1/1) (The yield containing the regioisomer at the double bond and the structural isomer: 84%, the target compound: the regioisomer at the double bond:exo form=79:19:2, The yield of the target compound only: 66%).

FT-IR (neat, cm$^{-1}$): 3627, 3393, 2980, 2937, 2362, 2056, 1732, 1679, 1520, 860, 774

$^1$H-NMR (CDCl$_3$, 400 MHz): δ 7.26 (d, J=8.0 Hz, 2H), 7.11 (d, J=8.0 Hz, 2H), 6.40 (d, J=15.6 Hz, 1H), 6.16 (dt, J=15.6, 7.2 Hz, 1H), 4.56-5.53 (m, 1H), 4.17-4.12 (m, 10H), 3.60-3.48 (m, 1H), 3.55 (s, 8H), 3.40-3.34 (m, 2H), 2.90-2.61 (m, 11H), 2.48 (ddd, J=14.4, 7.2, 7.0 Hz, 1H), 1.44 (s, 9H), 1.264 (t, J=6.8 Hz, 3H), 1.256 (t, J=6.8 Hz, 12H)

$^{13}$C-NMR (CDCl$_3$, 100 MHz): δ 171.9 (C), 170.5 (C×4), 155.2 (C), 137.4 (C), 135.1 (C), 131.0 (CH), 128.3 (CH×2), 126.0 (CH), 125.6 (CH×2), 78.3 (C), 63.3 (CH), 59.8 (CH$_2$×4), 59.6 (CH$_2$), 54.8 (CH$_2$×4), 52.9 (CH$_2$×2), 49.8 (CH$_2$×2), 41.4 (CH$_2$), 35.4 (CH$_2$), 33.2 (CH$_2$), 27.9 (CH$_3$×3), 14.0 (CH$_3$), 13.8 (CH$_3$×4)

EI-HRMS: m/z (M+Na$^+$) calculated value (C$_{40}$H$_{64}$N$_4$O$_{12}$Na): 815.4418, measured value: 815.4382

(3) Ethyl 2-[N,N-bis(2-{N',N'-bis[(ethoxycarbonyl)methyl]amino}ethyl)amino]-5-(4-{2-[(t-butoxy)carbonylamino]ethyl}phenyl)pentanoate

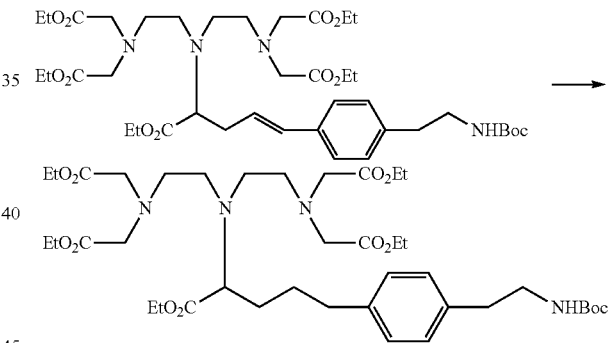

The pento-4-enolate compound (4.2 g, 5.30 mmol) obtained in the above Synthesis Example 2 (2) was dissolved in ethanol (40 mL). To the solution, 10% palladium carbon (0.28 g, 0.26 mmol) was added under an argon gas atmosphere. Then, the argon gas was replaced with a hydrogen gas. The mixture was stirred under a hydrogen gas atmosphere at room temperature for 11 hours. The mixture was filtered through Celite, and the filtrate was concentrated under reduced pressure. The target compound was obtained as a yellow oil from the concentrate by purification procedure using silica gel column chromatography (eluent: hexane/ethyl acetate=1/1) (yield: 97%).

FT-IR (neat, cm$^{-1}$): 3627, 3396, 2980, 2367, 2054, 1733, 1699, 1508, 1164, 868, 810, 775

$^1$H-NMR (CDCl$_3$, 400 MHz): δ 7.10 (s, 4H), 4.62-4.52 (m, 1H), 4.18-4.11 (m, 10H), 3.54 (s, 8H), 3.39-3.33 (m, 3H), 2.86-2.56 (m, 12H), 1.80-1.56 (m, 4H), 1.44 (s, 9H), 1.258 (t, J=7.2 Hz, 12H), 1.250 (t, J=7.2 Hz, 3H)

$^{13}$C-NMR (CDCl$_3$, 100 MHz): δ 172.9 (C), 170.8 (C×4), 155.5 (C), 139.9 (C), 136.0 (C), 128.4 (CH×2), 128.2 (CH×2), 78.6 (C), 63.4 (CH), 60.0 (CH$_2$×4), 59.7 (CH$_2$), 54.9

(CH₂×4), 53.4 (CH₂×2), 50.0 (CH₂×2), 41.5 (CH₂), 35.5 (CH₂), 34.9 (CH₂), 29.3 (CH₂), 28.1 (CH₃×3), 27.9 (CH₂), 14.1 (CH₃), 13.9 (CH₃×4)

EI-HRMS: m/z (M+H⁺) calculated value ($C_{40}H_{67}N_4O_{12}$): 795.4755, measured value: 795.4746

(4) 5-[4-(2-Aminoethyl)phenyl]-2-(N,N-bis{2-N',N'-bis[(carboxymethyl)amino]ethyl}amino)pentanoic acid

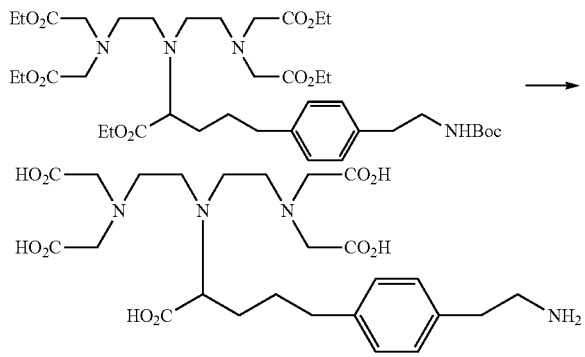

The compound obtained in the above Synthesis Example 2 (3) (500 mg, 0.63 mmol) was dissolved in a mixed solvent of THF/water=1/2 (1.5 mL). To the solution, 30% hydrochloric acid (1 mL) was added at room temperature. The mixture was stirred and heated under reflux for 14 hours. The mixture was freeze-dried. The target compound was obtained as a white powder from the lyophilized solid by purification procedure using high-performance liquid column chromatography (yield: 43%).

FT-IR (KBr, cm⁻¹): 3853, 3420, 2955, 2361, 1743, 1647, 1418, 1214, 899, 814, 667

¹H-NMR (D₂O, 400 MHz): δ 7.28 (d, J=7.2 Hz, 2H), 7.26 (d, J=7.2 Hz, 2H), 3.96 (s, 8H), 3.56-3.53 (m, 1H), 3.43 (t, J=6.8 Hz, 4H), 3.26 (t, J=6.9 Hz, 2H), 3.19-3.09 (m, 4H), 2.97 (t, J=6.8 Hz, 2H), 2.67 (t, J=6.8 Hz, 2H), 1.87-1.78 (m, 1H), 1.76-1.69 (m, 2H), 1.64-1.58 (m, 1H)

¹³C-NMR(O₂O, 100 MHz): δ 177.8 (C), 171.8 (C×4), 143.6 (C), 137.1 (C), 132.0 (CH×2), 131.9 (CH×2), 66.2 (CH), 58.0 (CH₂×4), 56.0 (CH₂×2), 49.5 (CH₂×2), 43.5 (CH₂), 37.1 (CH₂), 35.2 (CH₂), 30.5 (CH₂), 30.2 (CH₂)

ESI-HRMS m/z (M⁻) calculated value ($C_{25}H_{37}N_4O_{10}$): 553.2510, measured value: 553.2520

Synthesis Example 3

Ethyl 2-[bis(2-{bis[(ethoxycarbonyl)methyl]amino}ethyl)]-5-{4-[2-(2,5-dioxoazolinyl)ethyl]phenyl}pentanoate

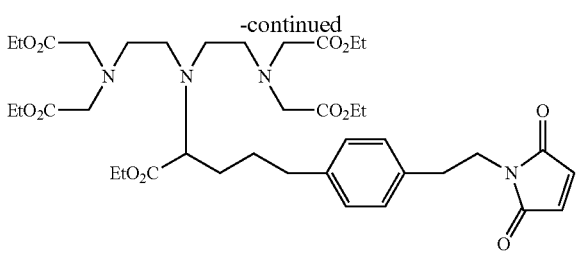

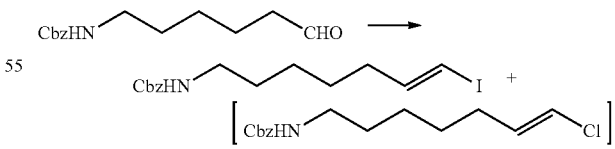

The compound obtained in the above Synthesis Example 2 (3) (270 mg, 0.34 mmol) was added to a mixed solution of 4N hydrochloride solution in ethyl acetate:dichloromethane=3:1 (2.0 mL). The mixture was stirred at room temperature for 4 hours, and then concentrated under reduced pressure. The concentrate was dissolved in dichloromethane (1.0 mL), and triethylamine (94.9 μL, 0.68 mmol) was added thereto. The mixture was stirred at room temperature for 5 minutes. Maleic anhydride (43.3 mg, 0.44 mmol) was added thereto, and the mixture was further stirred at room temperature for 2 hours. Then, the mixture was concentrated under reduced pressure. To the concentrate, DMF (1 mL), acetic anhydride (160.5 μL, 1.70 mmol) and sodium acetate (27.86 mg, 0.34 mmol) were added. The mixture was stirred at 100° C. for 18 hours. After 1N aqueous sodium hydroxide (2 mL) was added to the mixture, extraction procedure was carried out using ethyl acetate (20 mL) three times. The obtained extract was washed with saturated saline (20 mL), dried with anhydrous sodium sulfate, and concentrated under reduced pressure. The target compound was obtained as a yellow oil from the concentrate by purification procedure using silica gel column chromatography (eluent: hexane/ethyl acetate=1/1) (yield: 23%).

FT-IR (neat, cm⁻¹): 3624, 3465, 3095, 2981, 2861, 2365, 1713, 1515, 1445, 1407, 1368, 1190, 1029, 828, 759, 721, 696

¹H-NMR (CDCl₃, 400 MHz): δ 7.12-7.07 (dd, J=8.4, 2.4 Hz, 4H), 6.66 (s, 2H), 4.15 (q, J=7.2 Hz, 8H), 4.14 (q, J=7.2 Hz, 2H), 3.75-3.71 (m, 2H), 3.54 (s, 8H), 3.38-3.35 (m, 1H), 2.87-2.56 (m, 12H), 1.77-1.50 (m, 4H), 1.26 (t, J=7.2 Hz, 12H), 1.25 (t, J=7.2 Hz, 3H)

¹³C-NMR (CDCl₃, 100 MHz): δ 172.9 (C), 170.9 (C×4), 170.2 (C×2), 140.3 (C), 134.8 (C), 133.8 (CH×2), 128.5 (CH×2), 128.3 (CH×2), 63.7 (CH), 60.2 (C×4), 59.9 (CH₂), 55.1 (CH₂×2), 53.6 (CH₂×2), 50.2 (CH₂×2), 39.1 (CH₂), 35.2 (CH₂), 34.0 (CH₂), 29.5 (CH₂), 28.1 (CH₂), 14.3 (CH₃), 14.1 (CH₃×4)

ESI-HRMS: m/z (M+Na⁺) calculated value ($C_{39}H_{58}N_4O_{12}Na$): 797.3949, measured value: 797.3963

Synthesis Example 4

(1) Iodide

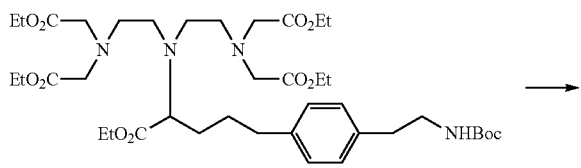

An aldehyde compound as a starting compound (described in U.S. Pat. No. 6,617,332, 2.4 g, 9.63 mmol) and iodoform (7.6 g, 19.3 mmol) were dissolved in THF (55 mL). The solution was added dropwise to a THF solution (80 mL) of chromium dichloride (7.1 g, 57.8 mmol) under an argon gas atmosphere over 1 minute. The mixture was stirred at room temperature under an argon gas atmosphere for 2 hours. Then, water (270 mL) was added thereto, and extraction procedure was carried out using a mixed solvent of ethyl acetate/hexane=1/1 (130 mL) three times. The obtained organic phase was washed with saturated saline, dried with anhydrous sodium sulfate, and concentrated under reduced pressure. A mixture of the target compound and a chloride as by-product was obtained from the concentrate by purification using silica gel column chromatography (eluent: hexane/ethyl acetate=3/1) (yield: 2.72 g). The mixture was analyzed by NMR; as a result, the mole ratio of the target compound and the by-product was 7:1. From the analysis result, the net amount of the target compound to be obtained was 2.46 g, 6.58 mmol, and the yield was 68%.

(2) Ethyl 2-[N,N-bis(2-{N',N'-bis[(ethoxycarbonyl)methyl]amino}ethyl)amino]-12-(t-butoxycarbonylamino)dodecanoate

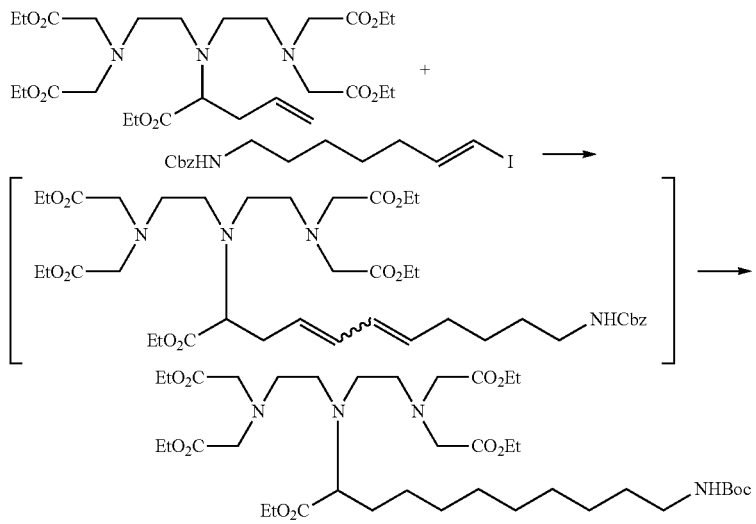

30

To a DMF solution (8 mL) containing the compound obtained in the above Synthesis Example 2(3) (615 mg, 1.07 mmol), the mixture containing the iodide and the chloride at the ratio of 7:1 (200 mg, the net weight of the iodide: 181 mg, 0.48 mmol) obtained in the above Synthesis Example 4(1), silver acetate (69 mg, 0.69 mmol) and palladium acetate (24 mg, 0.11 mmol) were added. The mixture was stirred at room temperature for 7 hours. The mixture was filtrate through silica gel. The filtrate was concentrated under reduced pressure. The above-described intermediate compound (311 mg, 0.38 mmol) was obtained from the concentrate by crudely-purification using silica gel column chromatography (eluent: hexane/ethyl acetate=3/2). The intermediate compound was dissolved in ethanol (2 mL). To the solution, $Boc_2O$ (99 mg, 0.46 mmol) and 20% palladium hydroxide (53 mg, 0.076 mmol) were dissolved under an argon gas atmosphere. The mixture was stirred under a hydrogen gas atmosphere at room temperature for 23 hours. The mixture was filtrated though Celite, and the filtrate was concentrated under reduced pressure. The target compound was obtained as a yellow oil from the concentrate by purification using silica gel column chromatography (eluent: hexane/ethyl acetate=3/2) (yield: 213 mg, 0.27 mmol, 56%).

FT-IR (neat, $cm^{-1}$): 3398, 2980, 2929, 2855, 1732, 1519, 1465, 1366, 1343, 1250, 1183, 1029, 989, 923, 866, 780, 725, 423

$^1$H-NMR ($CDCl_3$, 400 MHz): δ 4.52-4.50 (m, NH, 1H), 4.16 (q, J=7.2 Hz, 8H), 4.13 (q, J=7.2 Hz, 2H), 3.55 (s, 8H), 3.31 (t, J=7.2 Hz, 1H), 3.12-3.08 (m, —CH2-NHBoc, 2H), 2.86-2.61 (m, 8H), 1.44 (s, 9H), 1.20-1.28 (m, 33H)

$^{13}$C-NMR ($CDCl_3$, 100 MHz): δ 173.3 (C), 171.2 (C×4), 155.9 (C), 78.8 (C), 64.0 (CH), 60.3 ($CH_2$×4), 59.9 ($CH_2$), 55.2 ($CH_2$×4), 53.7 ($CH_2$×2), 50.4 ($CH_2$×2), 40.6 ($CH_2$), 30.0 ($CH_2$×2), 29.5 ($CH_2$×2), 29.4 ($CH_2$×2), 29.2 ($CH_2$), 28.4 ($CH_3$×3), 26.7 ($CH_2$), 26.4 ($CH_2$), 14.4 ($CH_3$), 14.2 ($CH_3$×4)

ESI-HRMS: m/z (M+H$^+$) calculated value ($C_{39}H_{73}N_4O_{12}$): 789.5225, measured value: 789.5186

Synthesis Example 5

Ethyl 2-[N,N-Bis(2-{N',N'-bis[(ethoxycarbonyl)methyl]amino}ethyl)amino]-5-{4-[2-({4-butyne-1-yl}carbonylamino)ethyl]phenyl}pentanoate

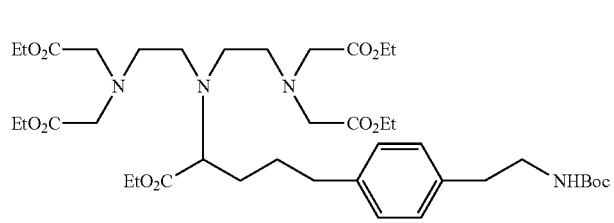
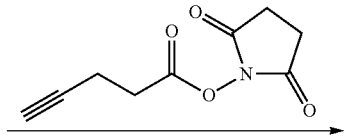
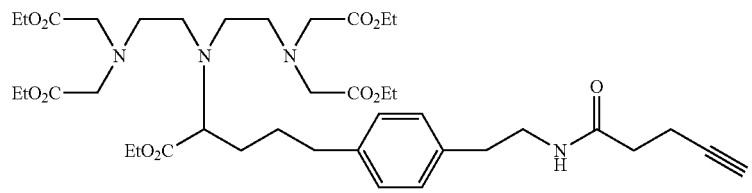

In accordance with to the description of Chen, G. et al., Langumuir, 25, pp. 2860-2864 (2009), 1-pentynoic acid N-oxysuccinimide was synthesized. The DTPA ester (100 mg, 0.126 mmol) obtained in the above Synthesis Example 2(3) is a mixed solution of 4N hydrochloride/ethyl acetate: dichloromethane=3:1 by volume (1.3 mL). The mixture was stirred at room temperature for 17 hours, and then concentrated under reduced pressure. The concentrate was dissolved in DMF (0.6 mL), and triethylamine (35.0 μL, 0.251 mmol) was added thereto. The mixture was stirred at room temperature for 5 minutes. Further, 1-pentynoic acid N-oxysuccinimide (28.0 mg, 0.143 mmol) was added thereto, and the mixture was stirred at room temperature for 14 hours. Next, a saturated aqueous solution of sodium bicarbonate (1 mL) was added to the mixture, and then extraction procedure was carried out using ethyl acetate (10 mL) three times. The extract was washed using saturated saline (10 mL), dried with anhydrous sodium sulfate and concentrated under reduced pressure. The target compound was obtained as a yellow oil from the concentrate by purification using silica gel column chromatography (eluent: hexane/ethyl acetate=1/2) (yield: 63.2 mg, 0.0816 mmol, 64.9%).

FT-IR (neat, $cm^{-1}$): 3300, 2981, 2119, 1733, 1653, 1539, 1447, 1370, 1195, 1028, 852, 808, 699

$^1$H-NMR (CDCl$_3$, 400 MHz): δ 7.11 (s, 4H), 5.68-5.66 (m, 1H), 4.15 (q, J=7.2 Hz, 8H), 4.13-4.09 (m, 2H), 3.55-3.50 (m, 2H), 3.54 (s, 8H), 3.39-3.36 (m, 1H), 2.83-2.74 (m, 8H), 2.67-2.58 (m, 4H), 2.51 (dt, J=2.8, 7.2 Hz, 2H), 2.35 (t, J=7.2 Hz, 2H), 1.95 (t, J=2.8 Hz, 1H), 1.78-1.70 (m, 4H), 1.26 (t, J=7.2 Hz, 12H), 1.25 (t, J=7.2 Hz, 3H)

$^{13}$C-NMR (CDCl$_3$, 100 MHz): δ 173.1 (C), 171.0 (C×4), 170.7 (C), 140.3 (C), 136.0 (C), 128.52 (CH×2), 128.46 (CH×2), 82.8 (C), 69.1 (CH), 63.6 (CH), 60.2 (CH$_2$×4), 59.9 (CH$_2$), 55.1 (CH$_2$×4), 53.6 (CH$_2$×2), 50.2 (CH$_2$×2), 40.5 (CH$_2$), 35.13 (CH$_2$), 35.08 (CH$_2$), 35.0 (CH$_2$), 29.4 (CH$_2$), 28.1 (CH$_2$), 14.7 (CH$_2$), 14.3 (CH$_3$), 14.1 (CH$_3$×4)

ESI-HRMS: m/z (M+Na$^+$) calculated value (C$_{40}$H$_{62}$N$_4$O$_{11}$Na): 797.4313, measured value: 797.4313

Synthesis Example 6

(1) 3-{(4-[N,N-Bis(2-{N',N'-bis[(ethoxycarbonyl)methyl]amino}ethyl)amino]4-ethoxycarbonyl1-buten-1-yl}phenylpropionic acid

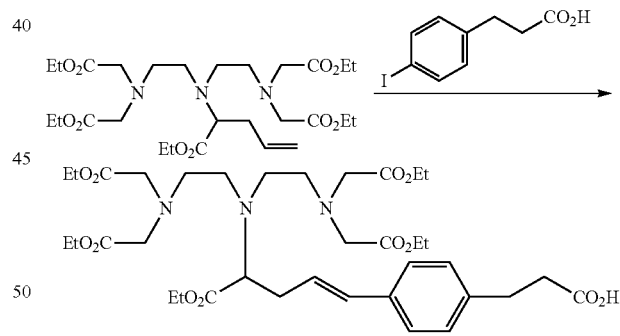

To a solution obtained by dissolving the DTPA ester (200 mg, 0.349 mmol) obtained in Synthesis Example 1 in a mixed solvent of DMF:water=10:1 by volume (1.1 mL), 3-(4-iodo)phenylpropionic acid (125.1 mg, 0.453 mmol) and diisopropylethylamine (93.3 μL, 0.523 mmol) was added at room temperature. The mixture was heated up to 60° C., and then bis(acetonitrile)dichloropalladium (9.0 mg, 0.0349 mmol) was thereto. The mixture was stirred at 60° C. for 4.5 hours. The mixture was filtered through silica gel, and the filtrate was concentrated under reduced pressure. The target compound was obtained as a yellow oil from the concentrate by purification procedure using silica gel column chromatography (eluent: hexane/ethyl acetate=1/2) (84 mg, 0.124 mmol, 36%).

FT-IR (neat, cm$^{-1}$): 3447, 2982, 2937, 2873, 1734, 1700, 1653, 1635, 1560, 1513, 1465, 1448, 1419, 1370, 1345, 1195, 1029, 970, 920, 853, 810, 733, 668

$^1$H-NMR (CDCl$_3$, 400 MHz): δ 7.25 (d, J=8.0 Hz, 2H), 7.12 (d, J=8.0 Hz, 2H), 6.40 (d, J=16.0 Hz, 1H), 6.15 (dt, J=16.0, 6.8 Hz, 1H), 4.17-4.12 (m, 10H), 3.55 (s, 8H), 3.50-3.47 (m, 1H), 2.95-2.60 (m, 13H), 2.48 (ddd, J=16.0, 7.6, 7.6 Hz, 1H), 1.28-1.23 (m, 15H)

$^{13}$C-NMR (CDCl$_3$, 100 MHz): δ 177.4 (C), 172.4 (C), 171.1 (C×4), 139.1 (C), 135.5 (C), 131.6 (CH), 128.2 (CH×2), 126.2 (CH), 126.1 (CH×2), 63.9 (CH), 60.3 (CH$_2$×4), 60.1 (CH$_2$), 55.1 (CH$_2$×4), 53.3 (CH$_2$×2), 50.1 (CH$_2$×2), 35.4 (CH$_2$), 33.5 (CH$_2$), 30.3 (CH$_2$), 14.3 (CH$_3$), 14.1 (CH$_3$×4)

ESI-HRMS: m/z (M+H$^+$) calculated value (C$_{36}$H$_{56}$N$_3$O$_{12}$): 722.3864, measured value: 722.3822

(2) 3-{4-[N,N-Bis(2-{N',N'-bis[(ethoxycarbonyl)methyl]amino}ethyl)amino]4-ethoxycarbonylbutane-1-yl}phenylpropionic acid

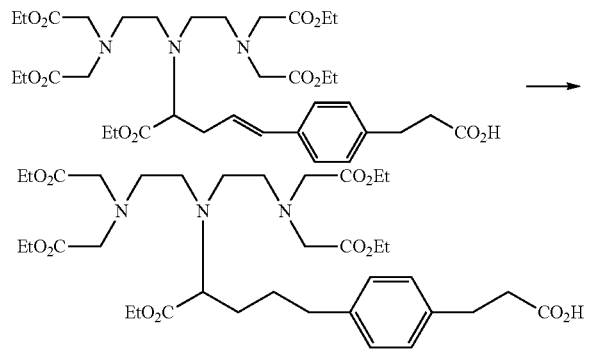

To the ethanol solution (1 mL) of the DTPA ester (93 mg, 0.137 mmol) obtained in the above Synthesis Example 6(1), palladium carbon (0.0137 mmol) was added under an argon gas atmosphere. The gas phase was replaced with a hydrogen gas, and then the mixture was stirred for 13.5 hours. The mixture was suction-filtered through Celite, and concentrated under reduced pressure. The target compound was obtained as a yellow oil from the concentrate by purification procedure using silica gel column chromatography (eluent: hexane/ethyl acetate=1/2) (yield: 89.3 mg, 0.123 mmol, 90%).

FT-IR (neat, cm$^{-1}$): 3584, 3446, 2981, 2936, 2869, 1732, 1515, 1446, 1417, 1372, 1347, 1298, 1198, 1097, 1027

$^1$H-NMR (CDCl$_3$, 400 MHz): δ 7.12 (d, J=8.4 Hz, 2H), 7.09 (d, J=8.4 Hz, 2H), 4.15 (q, J=7.2 Hz, 8H), 4.12-4.09 (m, 2H), 3.53 (s, 8H), 3.32-3.29 (m, 1H), 2.92 (t, J=7.6 Hz, 2H), 2.79-2.51 (m, 12H), 1.70-1.48 (m, 4H), 1.26 (t, J=7.2 Hz, 12H), 1.25 (t, J=7.2 Hz, 3H, OCH$_2$—CH$_3$)

$^{13}$C-NMR (CDCl$_3$, 100 MHz): δ 177.4 (C), 173.2 (C), 171.2 (C×4), 140.1 (C), 137.7 (C), 128.5 (CH×2), 128.2 (CH×2), 63.9 (CH), 60.4 (CH$_2$×4), 60.0 (CH$_2$), 55.2 (CH$_2$×4), 53.6 (CH$_2$×2), 50.2 (CH$_2$×2), 35.7 (CH$_2$), 35.2 (CH$_2$), 30.4 (CH$_2$), 29.5 (CH$_2$), 28.2 (CH$_2$), 14.4 (CH$_2$), 14.2 (CH$_3$×4)

ESI-HRMS: m/z (M+H$^+$) calculated value (C$_{36}$H$_{58}$N$_3$O$_{12}$): 724.4021, measured value: 724.4007

Synthesis Example 7

(1) N,N-Di(t-butoxycarbonyl)-O-[3-(4-iodo)phenyl]propylhydroxylamine

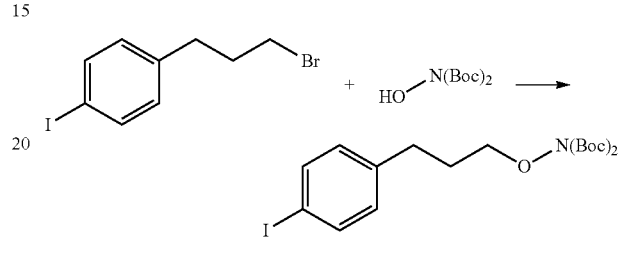

To a DMF solution (10 mL) of 3-[(4-iodo)phenyl]propyl-bromide (1.63 g, 6.990 mmol) and N,N-di(t-butoxycarbonyl)hydroxylamine (2.27 g, 6.99 mmol), DBU (1,8-diazabicyclo[5.4.0]undeca-7-ene) (1.15 mL, 7.68 mmol) was added. The mixture was stirred for 13 hours. Next, water (5 mL) was added thereto with cooling in ice, and extraction procedure was carried out using ethyl acetate (30 mL) three times. The extract was washed with saturated saline (20 mL), dried with anhydrous sodium sulfate, and concentrated under reduced pressure. The target compound was obtained from the concentrate by recrystallization using hexane (yield: 2.40 g, 5.03 mmol, 72%).

FT-IR (KBr, cm$^{-1}$): 3649, 3462, 2978, 2889, 2365, 2341, 1913, 1742, 1636, 1617, 1558, 1541, 1507, 1488, 1456, 1391, 1368, 1315, 1281, 1251, 1142, 1118, 1026, 1009, 907, 879, 837, 797, 747, 620, 507

$^1$H-NMR (CDCl$_3$, 400 MHz): δ 7.60 (d, J=8.4 Hz, 2H), 6.96 (d, J=8.4 Hz, 2H), 3.93 (t, J=6.2 Hz, 2H), 2.74-2.70 (m, 2H), 1.96-1.89 (m, 2H), 1.53 (s, 18H)

$^{13}$C-NMR (CDCl$_2$, 100 MHz): δ 150.2 (C×2), 141.2 (C), 137.4 (CH×2), 130.5 (CH×2), 90.9 (C), 83.7 (C×2), 75.2 (CH$_2$), 31.8 (CH$_2$), 29.7 (CH$_2$), 28.1 (CH$_3$×6)

ESI-HRMS: m/z (M+Na$^+$) calculated value (C$_{19}$H$_{28}$O$_5$Na): 500.0910, measured value: 500.0910

(2) Ethyl 2-[N,N-bis(2-{N',N'-bis[(ethoxycarbonyl)methyl]amino}ethyl)amino]-5-[4-{3-(O-t-butoxycarbonylamino)oxypropan-1-yl}phenyl]pent-4-enoate

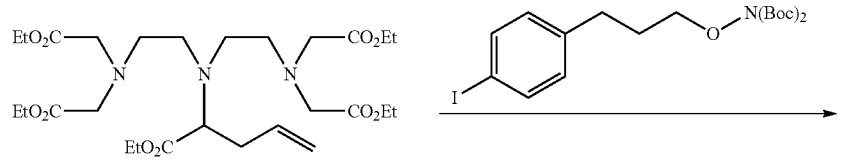

-continued

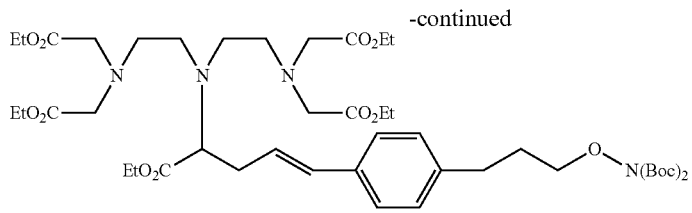

To a solution (3.3 mL) of the DTPA ester obtained in the above Synthesis Example 1 (688.1 mg, 1.20 mmol) in a mixed solution of DMF:water=10:1 by volume, a phenyl iodide compound (858.8 mg, 1.80 mmol) obtained in the above Synthesis Example 7(1) and diisopropylethylamine (308.7 µL, 1.80 mmol) were added at room temperature. The mixture was heated up to 60° C., and then bis(acetonitrile)dichloropalladium (35.4 mg, 0.120 mmol) was added thereto. The mixture was stirred at 60° C. for 8.5 hours. The mixture was filtered through silica gel, and the filtrate was concentrate under reduced pressure. The target compound was obtained as a yellow oil from the concentrate by purification procedure using silica gel column chromatography (eluent: hexane/ethyl acetate=1/1) (yield: 918.9 mg, 0.995 mmol, 83%).

FT-IR (neat, cm$^{-1}$): 3735, 3446, 2980, 2938, 2368, 2343, 1792, 1732, 1541, 1513, 1417, 1456, 1393, 1369, 1345, 1276, 1250, 1179, 1156, 1116, 1092, 972, 917, 882, 851, 796, 754, 717

$^1$H-NMR (CDCl$_3$, 400 MHz): δ 7.25 (d, J=8.0 Hz, 2H), 7.12 (d, J=8.0 Hz, 2H), 6.43 (d, J=15.6 Hz, 1H), 6.16 (ddd, J=15.6, 7.2, 7.2 Hz, 1H), 4.17-4.12 (m, 10H), 3.95 (t, J=6.4 Hz, 2H), 3.56 (s, 8H), 3.53-3.50 (m, 1H), 2.90-2.61 (m, 11H), 2.48 (ddd, J=14.4, 7.2, 7.2 Hz, 1H), 1.98-1.91 (m, 2H), 1.54 (s, 18H), 1.25 (t, J=7.2 Hz, 15H)

$^{13}$C-NMR (CDCl$_3$, 100 MHz): δ 172.3 (C), 171.0 (C×4), 150.0 (C×2), 140.28 (C), 135.2 (C), 131.5 (CH), 128.3 (CH×2), 126.0 (CH), 125.9 (CH×2), 83.5 (C×2), 75.5 (CH$_2$), 63.9 (CH), 60.3 (CH$_2$×4), 60.1 (CH$_2$), 55.2 (CH$_2$×4), 53.4 (CH$_2$×2), 50.3 (CH$_2$×2), 33.6 (CH$_2$), 32.0 (CH$_2$), 29.8 (CH$_2$), 28.0 (CH$_3$×6), 14.3 (CH$_3$), 14.1 (CH$_3$×4)

ESI-HRMS: m/z (M+H$^+$) calculated value (C$_{46}$H$_{75}$N$_4$O$_{15}$): 923.5229, measured value: 923.5198

(3) Ethyl 2-[N,N-bis(2-{N',N'-bis[(ethoxycarbonyl)methyl]amino}ethyl)amino]-5-[4-{3-(O—(N,N-t-butoxycarbonyl)amino)oxypropan-1-yl}phenyl]pentanoate To an ethanol solution (250 µL) of the DTPA ester (53.1 mg, 0.0575 mmol) obtained in the above Synthesis Example 7 (2), palladium carbon (0.00288 mmol) was added under an argon gas atmosphere. The gas phase was replaced with a hydrogen gas, and then the mixture was stirred for 17 hours. The mixture was suction-filtered though Celite, and the filtrate was concentrated under reduced pressure. The target compound was obtained as a yellow oil by purification procedure using silica gel column chromatography (eluent: hexane/ethyl acetate=1/1) (yield: 42.7 mg, 0.0462 mmol, 80%).

FT-IR (neat, cm$^{-1}$): 3630, 3552, 3456, 2980, 2373, 2346, 2054, 1902, 1792, 1731, 1514, 1456, 1417, 1393, 1369, 1344, 1249, 1029, 917, 851, 796, 754

$^1$H-NMR (CDCl$_3$, 400 MHz): δ 7.11 (d, J=8.0 Hz, 2H), 7.08 (d, J=8.0 Hz, 2H), 4.17-4.10 (m, 10H), 3.95 (t, J=6.4 Hz, 2H), 3.54 (s, 8H), 3.38 (t, J=6.8 Hz, 1H), 2.86-2.56 (m, 12H), 1.98-1.91 (m, 2H), 1.77-1.57 (m, 4H), 1.54 (s, 18H), 1.26 (t, J=7.2 Hz, 12H), 1.25 (t, J=7.2 Hz, 3H)

$^{13}$C-NMR (CDCl$_3$, 100 MHz): δ 173.2 (C), 171.1 (C×4), 150.2 (C×2), 139.8 (C), 138.9 (C), 128.3 (CH×2), 128.2 (CH×2), 83.6 (C×2), 75.6 (CH$_2$), 63.8 (CH), 60.4 (CH$_2$×4), 60.0 (CH$_2$), 55.2 (CH$_2$×4), 53.7 (CH$_2$×2), 50.3 (CH$_2$×2), 35.2 (CH$_2$), 31.9 (CH$_2$), 29.9 (CH$_2$), 29.7 (CH$_2$), 28.3 (CH$_2$), 28.0 (CH$_3$×6), 14.4 (CH$_3$), 14.2 (CH$_3$×4)

ESI-HRMS: m/z (M+Na$^+$) calculated value (C$_{46}$H$_{76}$N$_4$O$_{15}$Na): 947.5205, measured value: 947.5179

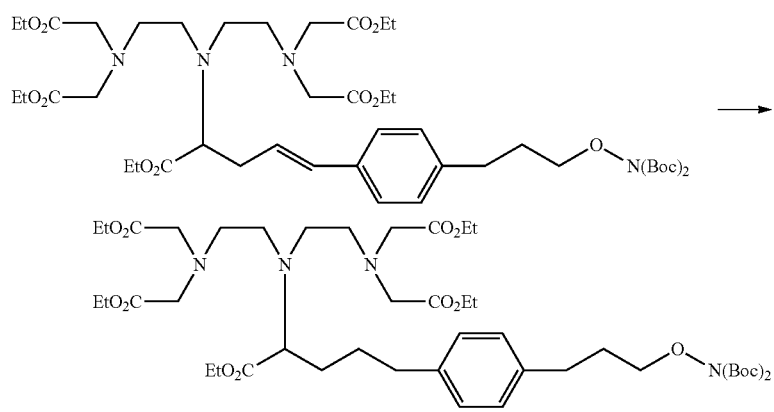

(4) Ethyl 2-[N,N-bis(2-{N',N'-bis[carbonic acid methyl]amino}ethyl)amino]-5-[4-{3-aminooxypropan-1-yl}phenyl]pentanoate

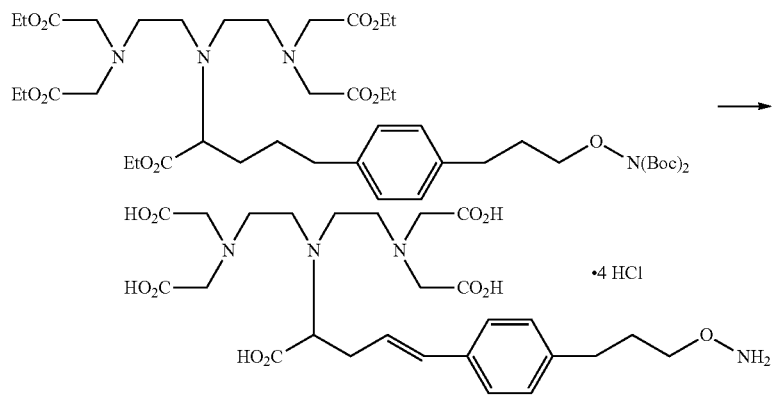

To a THF solution (8 mL) of the DTPA ester (400.0 mg, 0.432 mmol) obtained in the above Synthesis Example 7(3), a 4N aqueous solution of lithium hydroxide (594 μL) was added. The mixture was stirred at 50° C. for 19 hours. Further, a 4N hydrochloride solution in ethyl acetate (10 mL) was added thereto at 0° C., and the mixture was stirred at room temperature for 3.5 hours. Next, acetonitrile (4 mL) was added to the mixture. The target compound was obtained as a colorless powder by recrystallization using a mixed solvent of isopropanol/acetonitrile (yield: 258.7 mg, 0.342 mmol, 79%).

FT-IR (KBr, cm$^{-1}$): 3567, 3367, 2950, 2362, 2359, 2348, 1991, 1869, 1845, 1740, 1653, 1558, 1516, 1457, 1419, 1202, 1113, 1034, 953, 898, 873, 807, 715, 660, 609, 542, 489, 454

$^1$H-NMR (D$_2$O, 400 MHz): δ 7.25 (s, 4H), 4.07 (t, J=6.4 Hz, 2H), 4.03 (s, 8H), 3.64-3.60 (m, 1H), 3.44 (t, J=6.0 Hz, 4H), 3.20-3.12 (m, 4H), 2.71 (t, J=7.6 Hz, 2H), 2.66 (t, J=6.8 Hz, 2H), 2.02-1.95 (m, 2H), 1.87-1.82 (m, 1H), 1.79-1.71 (m, 2H), 1.70-1.61 (m, 1H)

$^{13}$C-NMR (D$_2$O, 100 MHz): δ 177.7 (C), 172.5 (C×4), 142.7 (C), 141.9 (C), 131.7 (CH×2), 131.6 (CH×2), 77.6 (CH$_2$), 66.3 (CH), 58.5 (CH$_2$×4), 55.7 (CH$_2$×2), 49.6 (CH$_2$×2), 37.1 (CH$_2$), 33.3 (CH$_2$), 31.6 (CH$_2$), 30.5 (CH$_2$), 30.3 (CH$_2$)

ESI-HRMS: m/z (M+H$^+$) calculated value (C$_{26}$H$_{39}$N$_4$O$_{11}$): 583.2615, measured value: 583.2599

Elemental analysis: calculated value (C$_{26}$H$_{44}$N$_4$O$_{11}$C$_{14}$.5H$_2$O)—C, 41.23; H, 6.25; N, 7.40. measured value—C, 41.02; H, 6.37; N, 7.53

As the above-described Examples, it become possible by the present invention process that one allyl group is regiospecifically and efficiently bound to a diethylenetriaminepentaacetic acid pentaester on very simple condition. In addition, it is possible that a linker structure having a reactive functional group or a protected reactive functional group is easily bound to the diethylenetriaminepentaacetic acid derivative obtained by the present invention process by a condensing reaction using a metal catalyst. It is possible that a substituent for improving a retention property in blood and specificity to an intended organ is bound through the reactive functional group in the linker structure. Therefore, the present invention is very useful to enable an industrial large-scale production of a contrast agent for MRI which has a retention property in blood and specificity to an intended organ.

Industrial Applicability

According to the present invention process, a reactive functional group can be efficiently bound to the specific position of a DTPA ester on an amazingly simple condition compared with conventional processes. In addition, the DTPA derivative obtained by the present invention process is very useful, since a substituent for improving a retention property in blood and specificity to an intended organ can be further bound through the reactive functional group.

Therefore, the present invention is industrially very useful to enable an industrial large-scale production of a contrast agent for MRI which has a retention property in blood and specificity to an intended organ.

The invention claimed is:

1. A process for preparation of a diethylenetriaminepentaacetic acid derivative;
wherein the diethylenetriaminepentaacetic acid derivative is represented by the following formula (I):

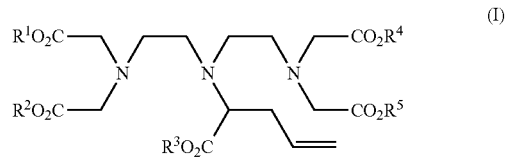

wherein R$^1$ to R$^5$ are independently C$_{1-6}$ alkyl groups;
comprising the steps of:
reacting a diethylenetriaminepentaacetic acid pentaester represented by the following formula (II) with a halogenated ally compound represented by the following formula (III) in an aprotic solvent:

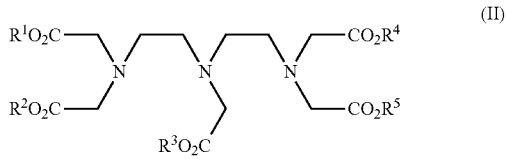

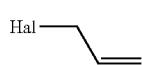

(III)

wherein $R^1$ to $R^5$ have the same meaning as the above; and "Hal" is a halogen atom;

removing the excess halogenated ally compound (III); and reacting a reaction product of the diethylenetriaminepentaacetic acid pentaester (II) and the halogenated ally compound (III) with a base in a solvent.

2. The preparation process according to claim 1, wherein the halogenated ally compound (III) of not less than 7 times by mole relative to the diethylenetriaminepentaacetic acid pentaester (II) is reacted.

3. The preparation process according to claim 1, wherein a carbonate or a hydrogencarbonate of an alkali metal or an alkaline earth metal is used as the base.

4. The preparation process according to claim 1, wherein dimethylformamide or dimethylacetamide is used as the aprotic solvent.

5. A diethylenetriaminepentaacetic acid derivative represented by the following formula (I):

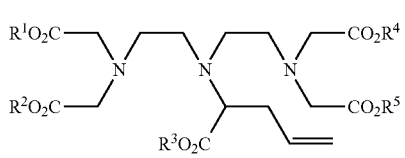

(I)

wherein $R^1$ to $R^5$ are independently $C_{1-6}$ alkyl groups.

6. A gadolinium complex precursor represented by the following formula (IV):

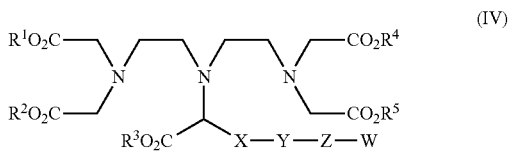

(IV)

wherein $R^1$ to $R^5$ are independently $C_{1-6}$ alkyl groups;

X is $-(CH_2)_3-$ or $-CH_2-CH=CH-$;

Y is a $C_{6-12}$ arylene group, $-CH=CH-$ or $-(CH_2)_2-$;

Z is a $C_{1-6}$ alkylene group, an amino group, an ether group, a carbonyl group, an ester group, an amide group, a urea group, or a group formed by linearly-bonding two or more groups selected from the group consisting of a $C_{1-6}$ alkylene group, an amino group, an ether group, a carbonyl group, an ester group, an amide group, a urea group; and W is $-CH=CH_2$, $-C\equiv CH$, an amino group, a carboxy group, an active amide group, an active ester group or a halogen atom.

7. The preparation process according to claim 2, wherein a carbonate or a hydrogencarbonate of an alkali metal or an alkaline earth metal is used as the base.

8. The preparation process according to claim 2, wherein dimethylformamide or dimethylacetamide is used as the aprotic solvent.

9. The preparation process according to claim 3, wherein dimethylformamide or dimethylacetamide is used as the aprotic solvent.

* * * * *